United States Patent [19]

Kuerzinger et al.

[11] Patent Number: 4,783,317
[45] Date of Patent: Nov. 8, 1988

[54] APPARATUS FOR THE MONITORING AND REGULATION OF MATERIAL CONCENTRATIONS IN CHEMICAL PROCESSES (II)

[75] Inventors: Karl Kuerzinger, Hanau; Peter Wachendoerfer, Frankfurt, both of Fed. Rep. of Germany

[73] Assignee: Degussa Aktiengesellschaft, Frankfurt am Main, Fed. Rep. of Germany

[21] Appl. No.: 903,624

[22] Filed: Sep. 2, 1986

[30] Foreign Application Priority Data

Sep. 21, 1985 [DE] Fed. Rep. of Germany ....... 8527072

[51] Int. Cl.⁴ .................. G01N 27/00; G01N 25/20
[52] U.S. Cl. ........................... 422/68; 422/51; 422/83; 422/95; 436/147; 436/160; 73/25
[58] Field of Search ............... 422/51, 68, 83, 95; 436/147, 160; 73/25

[56] References Cited

U.S. PATENT DOCUMENTS

| | | | |
|---|---|---|---|
| 1,643,155 | 9/1927 | Eisenschitz | 422/95 |
| 2,004,611 | 6/1935 | Kleinfelder | 422/83 |
| 3,558,280 | 1/1971 | Panson | 436/136 |
| 3,957,441 | 5/1976 | Baba | 436/160 |
| 4,344,917 | 8/1982 | Schorno | 422/83 |
| 4,518,566 | 5/1985 | Sorenson | 436/147 |
| 4,555,491 | 11/1985 | Spurlin et al. | 436/120 |

Primary Examiner—David L. Lacey
Assistant Examiner—Lori-Ann Johnson
Attorney, Agent, or Firm—Beveridge, DeGrandi & Weilacher

[57] ABSTRACT

To regulate and monitor material concentrations, e.g., sodium chlorite or hydrogen peroxide, measuring cells are employed in which these substances are reacted to completion with another substance, e.g., sulfur dioxide, in an exothermal reaction. The resulting temperature rise is then a measure for the concentration. A simple measuring cell includes a pipe section provided at both ends with mounting devices for mounting in the delivery line conveying the reaction medium. There is mounted in this pipe section a U-shaped pipe section which is open at both ends and has a smaller diameter, and whose two arms extend into the pipe section with a larger diameter. The center section of, and parallel to, is located outside of the larger pipe and is provided with a thermal insulation, a supply line for the reacting substance, and a temperature sensor.

6 Claims, 1 Drawing Sheet

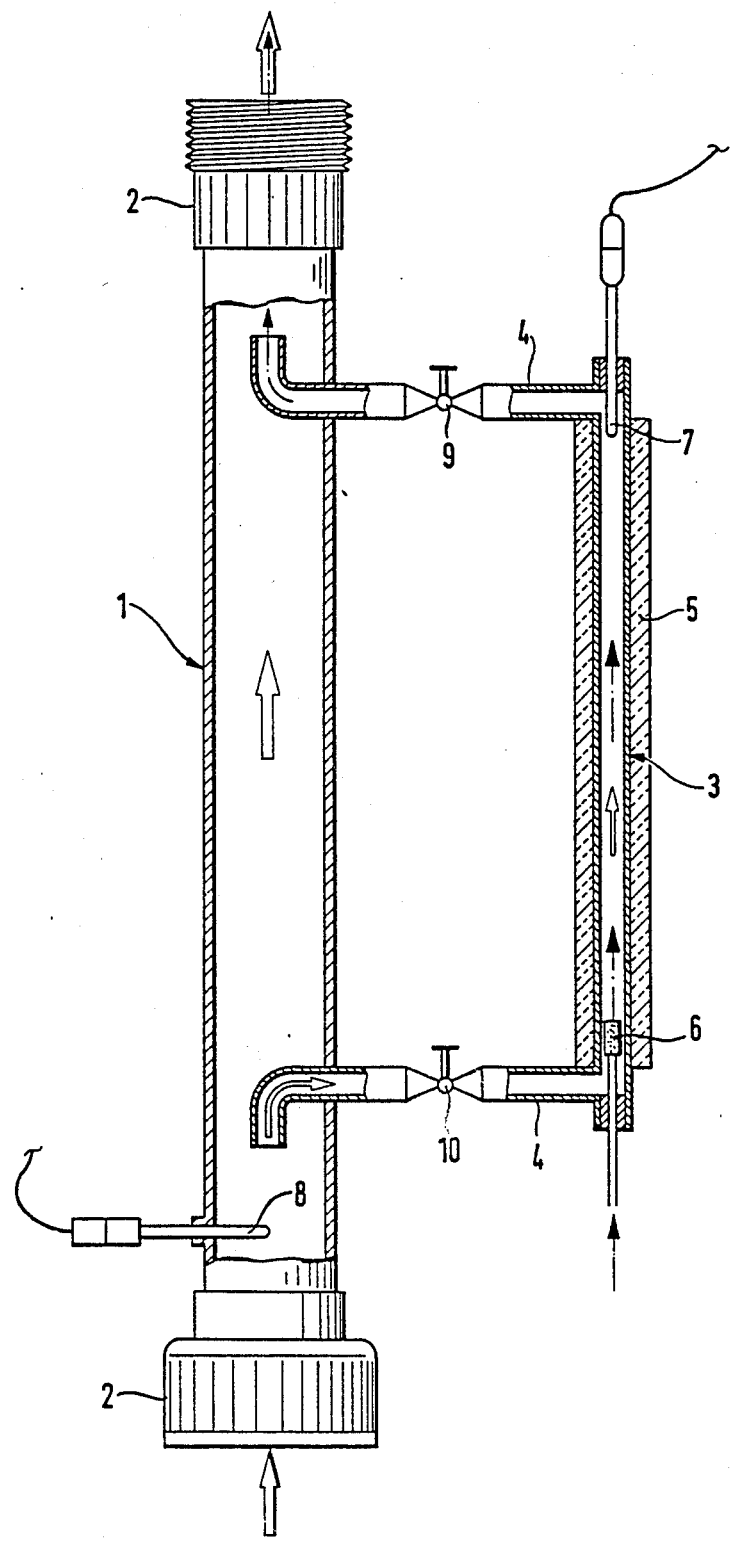

APPARATUS FOR THE MONITORING AND REGULATION OF MATERIAL CONCENTRATIONS IN CHEMICAL PROCESSES (II)

Reference is made to related commonly assigned U.S. application, Ser. No. 897,945 filed Aug. 19, 1986.

BACKGROUND OF THE INVENTION

The invention relates to a device for the monitoring and regulation of material concentrations in chemical process, said substances reacting to completion in an exothermal reaction with othe substances, by measuring the temperature rise in this reaction. The apparatus comprises a measuring cell with supply lines for the reaction medium and the reacting substance, a discharge line, and temperature sensors. The apparatus serves in particular for determining and monitoring hydrogen peroxide and chlorite concentrations in scrubbing solutions for scrubbing the flue gases of, for example, waste-incineration plants or large capacity firing systems.

In many continuous and discontinuous chemical processes which operate with such substances as hydrogen peroxide, sodium chlorite or other oxidizing and reducing agents, it is necessary to monitor the concentration of these substances by continuously measuring and, if necessary, adjusting the amounts and concentration. This is also particularly true for modern processes of flue gas scrubbing, in which there are removed from the flue gases substances such as sulfur dioxide by means of solutions containing hydrogen peroxide, or nitrogen oxides by means of solutions containing sodium chlorite.

Aqueous sodium chlorite solutions have recently been used to convert the nitrogen monoxide contained in the flue gases of waste incineration plants to nitrogen dioxide by wet scrubbing. In acidic chlorite solutions, more or less free chlorine dioxide, which is extremely explosive, is formed depending on the pH. Thus, it is important continuously to monitor and control the chlorite concentration in such solutions.

West German Patent No. 34 37 624 discloses an apparatus with which hydrogen peroxide concentrations in liquid reaction media can be monitored and adjusted by reacting to completion with sulfur dioxide in a measuring cell a partial stream of the hydrogen peroxide-containing solution and measuring the temperature rise resulting from the heat of reaction. The temperature rise is a measure of the heat production and thus also a measure of the hydrogen peroxide concentration in the reaction medium. Similarly, the concentrations in aqueous solutions of other oxidizing agents, such as sodium chlorite, can also be measured with sulfur dioxide or other reducing agents.

The apparatus of the invention comprises a thermally insulated measuring cell, which at one end has a separate supply line for a partial stream of the oxidizing reaction medium and a separate supply line for the reacting substance, e.g., sulfur dioxide and, at the other end, a discharge line. Temperature sensors for measuring the inlet and outlet temperatures of the liquids are installed on the supply lines and on the discharge line.

This measuring cell must be connected to a partial stream line of the reaction medium and, thus, it also requires additional supply lines, metering devices, valves and/or pumps. Thus, direct connection to the delivery line of the reaction medium is desirable, said line, for example, delivering the scrubbing liquid from the bottom sump to the scrubber head of an absorption column.

SUMMARY OF THE INVENTION

Accordingly, the present invention had as its object the development of an apparatus for determining and monitoring substance concentrations in liquid media, such substances reacting to completion with other substances in an exothermal reaction, by measuring the temperature rise in this reaction. The apparatus comprises a measuring cell with supply lines for the reaction medium and the reacting substance, a discharge line, and temperature sensors, which can be operated without additional lines and delivery components.

According to the invention, this object is attained by providing an apparatus comprising a pipe section with approximately the same diameter at both ends as the delivery line conveying the reaction medium, with mounting devices for installation in the delivery line. Axially positioned on said pipe section is a smaller-diameter pipe section which is open at both ends, whereby the two arms (14) of the U-shaped pipe section bent away at right angles at their open ends extend into the pipe section with the larger diameter. The center piece of the U-shaped pipe section is located outside and is provided with a thermal isolation. In addition, the apparatus has a supply line for the reacting substance and a temperature sensor for measuring the temperature rise of the mixture.

Preferably, the diameter of the U-shaped pipe section is at most half as large as that of the pipe section mounted in a delivery line. In this way, it is ensured that only a small partial stream of the reaction medium flows through the U-shaped pipe section which serves as the measuring cell.

The apparatus incorporating the invention can be mounted without difficulty in a delivery line conveying the reaction medium. It does not require any additional lines, valves or pumps in order to produce a partial stream of reaction medium necessary for the measurement. The mounting devices can, for example, be constructed as a flange or screw connection.

BRIEF DESCRIPTION OF THE DRAWING

The invention is further illustrated in the drawing which shows a schematic representation of an exemplary embodiment of the apparatus of the invention.

DETAILED DESCRIPTION OF THE DRAWING

In further detail, the apparatus of the invention comprises a pipe section (1), whose diameter corresponds approximately to that of the delivery line in which it is mounted by means of mounting devices (2) at both ends of the pipe section. On this pipe section (1) there is axially positioned a U-shaped pipe section (3) which is open at both ends and has a smaller diameter than pipe (1). This U-shaped pipe section (3) has two arms(4) bent away at right angles on their open ends and each extends into the larger-diameter pipe section (1) in such a way that a partial stream of the reaction medium can flow through this U-shaped pipe section (3). The center piece or section of U-shaped pipe section (3) is located outside of, and generally parallel to, the pipe section (1). It is provided with a thermal insulation (5), a supply line (6) for the reacting substance, and a temperature sensor (7). The temperature of the incoming reaction medium, e.g., an aqueous solution of sodium chlorite or hydrogen peroxide, is measured by a temperature sensor (8) when it enters the pipe section (1).

The actual measuring cell in the U-shaped pipe section (3) is formed by the central parallel section between the supply line (6) for the reacting substance, e.g., gaseous sulfur dioxide, and the temperature sensor (7), which measures the temperature rise as a result of the ongoing exothermal reaction, which is a measure for the concentration of the sodium chlorite or hydrogen peroxide. The temperature sensor may be any conventional type. The amount of the partial current of the reaction medium in the U-shaped pipe section (3) can additionally be controlled by means of the valves (9, 10) which may be conventional. When these valves are shut off, the U-shaped part can take off without interruption from the main delivery line and, e.g., replaced in the event of a defect.7 The supply line (6) is of any conventional design and may contain a diffusing element at its end to disperse the reacting substance into the reaction medium.

Further variations and modifications of the invention will be apparent to those skilled in the art from the foregoing and are intended to be encompassed by the claims appended hereto.

We claim:

1. An apparatus for the monitoring and regulation of material concentrations in a reaction medium by measuring the temperature rise of the reaction medium in an exothermal reaction with a substance which chemically reacts with the reaction medium upon contact, comprising: a first pipe section of a certain diameter; mounting means provided at each end of said first pipe section for mounting said first pipe section at one of its ends to a delivery line conveying the reaction medium and at its other end to a discharge line, the delivery line having a diameter approximately equal to the diameter of said first pipe section; a second pipe section including a center section, a first arm section and a second arm section, said first arm section having a first free and open end and a second end integrally secured to one end of said center section, the second arm section having a first free and open end and a second end integrally secured to the other end of said center section, said center section being disposed externally adjacent said first pipe section and in axial alignment therewith, said first and second arm sections extending away from said center section such that the free and open end of each of said arm sections extends into said first pipe section, the free and open end of each of said arm sections being bent away from said center section within said first pipe section; said apparatus further comprising thermal insulation encompassing the center section of said second pipe section; a supply line for the substance which chemically reacts with the reaction medium upon contact and a first and second temperature sensor, said supply line and said first temperature sensor both connected to said second pipe section, said first temperature sensor positioned and arranged to measure the temperature of the reaction medium after the reaction medium comes in contact with the substance which chemically reacts with it, and said second temperature sensor positioned and arranged to measure the temperature of the reaction medium before the reaction medium comes in contact with the substance which chemically reacts with it.

2. An apparatus as set forth in claim 1, wherein said second temperature sensor is secured to said first pipe section at a position between the end of said first pipe section which first comes into contact with the reaction medium flowing therethrough and the free open end of the second arm section of said second pipe section which first comes into contact with the reaction medium.

3. An apparatus as set forth in claim 1, wherein said supply line for the substance which reacts with the reaction medium upon contact has a dispersion nozzle connected to its end and the dispersion nozzle is positioned so as to be at the end of the center section of said second pipe section which first comes into contact with the reaction medium flowing therethrough.

4. An apparatus as recited in claim 3, wherein said first temperature sensor is positioned at the opposite end of the center section of said second pipe section.

5. An apparatus as recited in claim 1, further comprising at least one shut off valve on said second pipe section.

6. The apparatus as set forth in claim 1, wherein the diameter of said second pipe section is at most half as large as the diameter of said first pipe section.

* * * * *